(12) United States Patent
Kim

(10) Patent No.: US 9,005,917 B2
(45) Date of Patent: Apr. 14, 2015

(54) VARIABLE COLOR TWO-PHOTON FLUORESCENT PROBE, METHOD FOR IMAGING THIOL ACTIVATION IN MITOCHONDRION USING SAME, AND METHOD FOR MANUFACTURING THE VARIABLE COLOR TWO-PHOTON FLUORESCENT PROBE

(75) Inventor: Hwan Myung Kim, Gyeonggi-do (KR)

(73) Assignee: Ajou University Industry-Academic Cooperation Foundation, Suwon-Si, Gyeonggi-Do (KR)

( * ) Notice: Subject to any disclaimer, the term of this patent is extended or adjusted under 35 U.S.C. 154(b) by 0 days.

(21) Appl. No.: 14/118,053

(22) PCT Filed: Oct. 17, 2011

(86) PCT No.: PCT/KR2011/007697
§ 371 (c)(1),
(2), (4) Date: Dec. 26, 2013

(87) PCT Pub. No.: WO2012/157821
PCT Pub. Date: Nov. 22, 2012

(65) Prior Publication Data
US 2014/0127737 A1    May 8, 2014

(30) Foreign Application Priority Data
May 16, 2011    (KR) .................. 10-2011-0045878

(51) Int. Cl.
| | | |
|---|---|---|
| *C07F 9/653* | (2006.01) | |
| *C07F 9/6539* | (2006.01) | |
| *G01N 33/50* | (2006.01) | |
| *G01N 33/58* | (2006.01) | |
| *C07D 235/18* | (2006.01) | |
| *C07D 263/58* | (2006.01) | |
| *C07D 277/68* | (2006.01) | |

(52) U.S. Cl.
CPC .............. *C07F 9/6539* (2013.01); *C07F 9/653* (2013.01); *C07D 235/18* (2013.01); *G01N 33/582* (2013.01); *G01N 33/5005* (2013.01); *C07D 263/58* (2013.01); *C07D 277/68* (2013.01); *G01N 33/5079* (2013.01)

(58) Field of Classification Search
CPC ... C07F 9/653; C07F 9/6539; G01N 33/5079; G01N 33/582
See application file for complete search history.

(56) References Cited

PUBLICATIONS

Lim et al. "Ratiometric Detection of Mitochondrial Thiols with a Two-Photon Fluorescent Probe" Journal of the American Chemical Society, 2011, vol. 133, pp. 11132-11135 and S1-S16.*
International Preliminary Report on Patentability for PCT/KR2011/007697 mailed on Nov. 28, 2013.
Written Opinion of the International Searching Authority for PCT/KR2011/007697 mailed on May 29, 2012.
Jun Han L., Chang Su L., Yu Shun T., Ji Hee H., Bong Rae C., "A Two-Photon Fluorescent Probe for Thiols in Live Cells and Tissues", JACS Communications, Oct. 28, 2009, 1216-1217, vol. 132, No. 4, American Chemical Society.
M.K. Slodzinski, A.M. Aon, B.O'Rourke, "Glutathione Oxidation as a Trigger of Mitochondrial Depolarization and Oscillation in Intact Hearts", NIH Public Access, Nov. 2008, 650-660, vol. 45, No. 5, J Mol Cell Cardiol.
Katey M.L., Miguel A. A., Sonia C., Brain O., Carsten T.M., David L., "Diallyl disulphide depletes glutathione in Candida albicans: oxidative stress-mediated cell death studied by two-photon microscopy", NIH Public Access, Apr. 11, 2008, 695-706, vol. 24, No. 8, Yeast.
Xiaojian S., Andy Y.S., Helge C.J., Heidi E., Ping L., Timothy H.M., "Two-photon Imaging of Glutathione Levels in Intact Brain Indicates Enhanced Redox Buffereing in Developing Neurons and Cells at the Cerebrospinal Fluid and Blood-Brain Interface", Jun. 23, 2006, 17420-17431, vol. 281, No. 25, Journal of Biological Chemistry.
International Search Report mailed May 29, 2012 for PCT/KR2011/007697.

* cited by examiner

*Primary Examiner* — Joseph Kosack
(74) *Attorney, Agent, or Firm* — Lowe Hauptman & Ham, LLP

(57) ABSTRACT

The present invention relates to a two-photon fluorescent probe, more particularly a two-photon fluorescent probe represented by Formula 1, a method for preparing same and a method for imaging thiols in mitochondria using same. The two-photon fluorescent probe according to the present invention, having two probes introduced in one molecule, can selectively dye mitochondria and emit intense fluorescence by reacting with thiols. Accordingly, it can be used to image the distribution and activation of thiols in a living cell or an intact living tissue.

3 Claims, 8 Drawing Sheets

VARIABLE COLOR TWO-PHOTON FLUORESCENT PROBE, METHOD FOR IMAGING THIOL ACTIVATION IN MITOCHONDRION USING SAME, AND METHOD FOR MANUFACTURING THE VARIABLE COLOR TWO-PHOTON FLUORESCENT PROBE

CROSS-REFERENCE TO RELATED APPLICATIONS

This application claims priority under 35 U.S.C. §119 to Korean Patent Application No. 10-2011-0045878, filed on May 16, 2011, in the Korean Intellectual Property Office, the disclosure of which is incorporated herein by reference in its entirety.

BACKGROUND (a) Technical Field

The present invention relates to a ratiometric fluorescent probe which is selectively targeted to mitochondria, the representative active cellular organelles, and whose color of two-photon fluorescence changes upon binding to thiols, more particularly to a two-photon fluorescent probe capable of imaging the activity of thiols existing inside mitochondria with high sensitivity and selectivity by two-photon microscopy of low energy excitation source in real time and a method for preparing same.

(b) Background Art

Intracellular thiol derivatives (cysteine (Cys), homocysteine (Hcy) and glutathione (GSH)) play vital roles in biological activities. In particular, the thiol (RSH) derivatives in mitochondria play a key role in maintaining protein structure and redox balance through equilibrium with the disulfide (RSSR) forms. It is known that the ratio of thiol (RSH) to disulfide (RSSR) derivatives in the mitochondria is maintained at 100:1 or higher. A disruption of the balance may lead to severe cell damage and death.

To understand the roles of thiols, many one-photon fluorescent probes have been developed using fluorescein, rhodamine, green fluorescent protein (GFP), etc. as a fluorophore. However, most of these one-photon probes are problematic in that they require short excitation wavelengths (<500 nm), limiting their use in tissue imaging because of shallow penetration depth (<100 μm), photobleaching, cellular autofluorescence, and so forth. Two-photon microscopy (TPM) has been presented to solve these problems. Two-photon microscopy provides a number of advantages over one-photon microscopy, including increased penetration depth, localized excitation and prolonged observation time, because it utilizes two near-infrared photons of lower energy for excitation.

The probe market is increasing every year globally and about 4,000 one-photon fluorescent probes are commercially available. However, the number of two-photon probes developed thus far is only about 10, and, in particular, there is no two-photon fluorescent probe capable of selectively detecting thiols present in the mitochondria.

SUMMARY

The inventors of the present invention have researched to develop a two-photon fluorescent probe capable of solving the short excitation wavelength problem of the existing one-photon fluorescent probe and selectively detecting thiols in mitochondria. As a result, they have developed a two-photon fluorescent probe (SSH-Mito) capable of selectively detecting thiols existing in mitochondria.

The present invention is directed to providing a two-photon fluorescent probe appropriate for selectively dyeing mitochondria and imaging the selectivity and activity of thiols.

The present invention is also directed to providing a method for preparing the two-photon fluorescent probe.

The present invention is also directed to providing a method for selectively imaging the distribution and activity of thiols inside mitochondria in a living cell or tissue using the two-photon fluorescent probe.

In an aspect, the present invention provides a two-photon fluorescent probe represented by Formula 1:

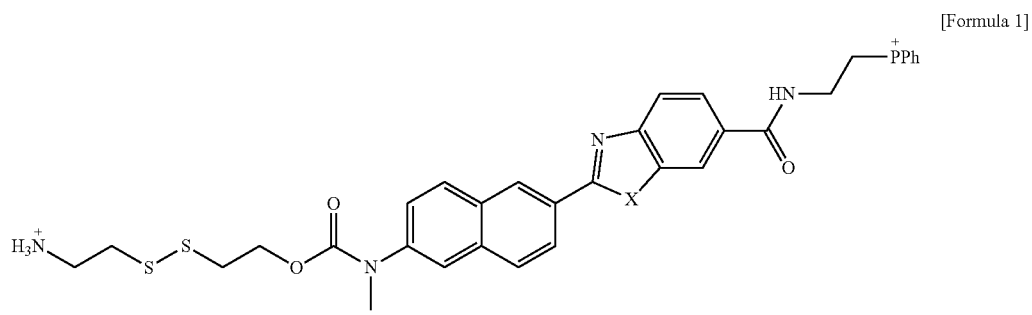

[Formula 1]

wherein X is S or O.

In another aspect, the present invention provides a method for preparing a two-photon fluorescent probe represented by Formula 1, including:

(a) dissolving a compound represented by Formula 2 and a compound represented by Formula 3 in nitrobenzene and stirring the resulting mixture to obtain a compound represented by Formula 4;

(b) reacting the compound represented by Formula 4 with a compound represented by Formula 5 to obtain a compound represented by Formula 6;

(c) mixing the compound represented by Formula 6 with pyridine and a compound represented by Formula 7, adding N,N-dimethylaminopyridine (DMAP) and stirring the resulting mixture to obtain a compound represented by Chemical Formula; and (d) dissolving the compound represented by Formula 8 in a solvent, stirring and evaporating the solvent:

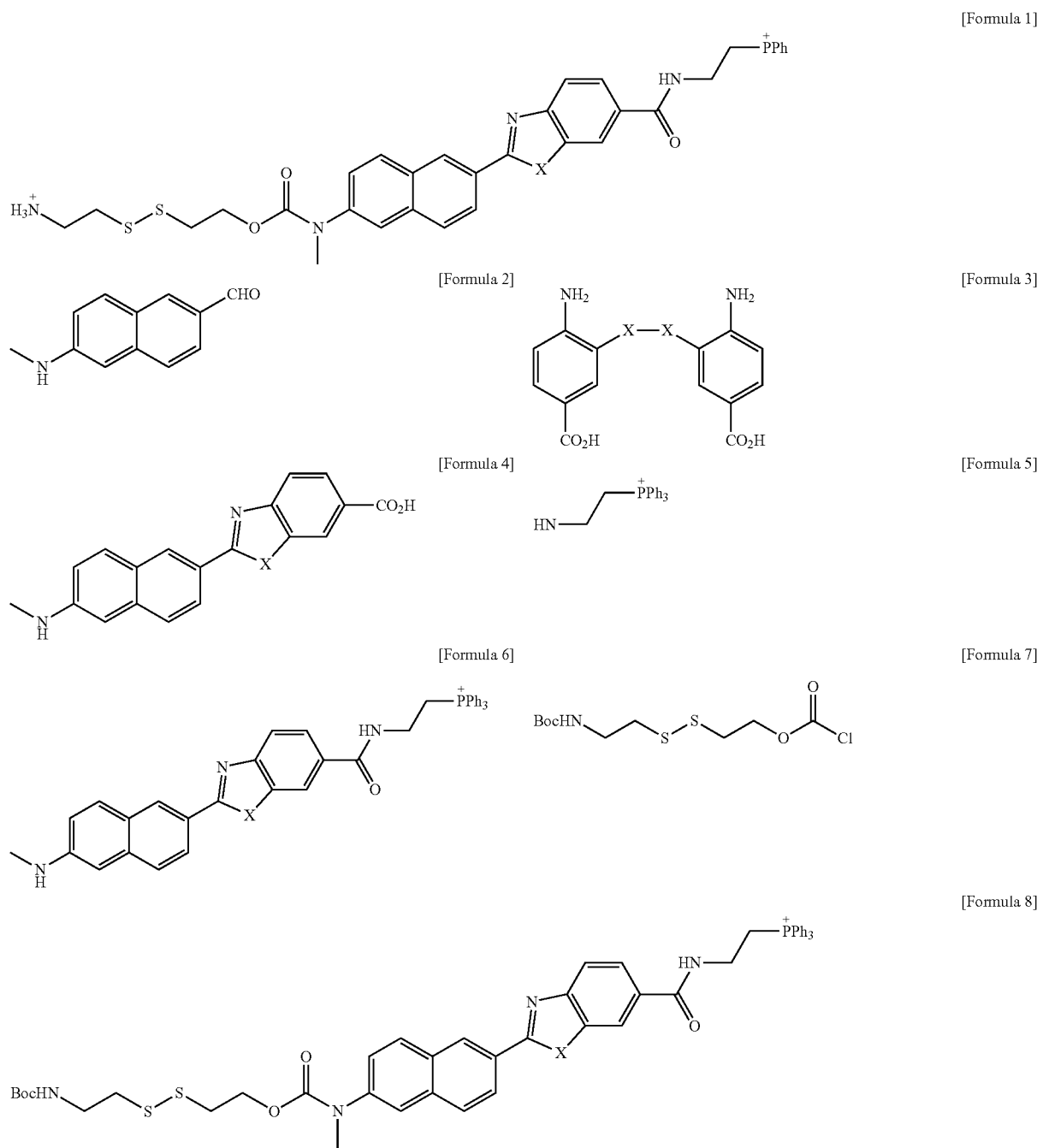

wherein X is S or O.

In another aspect, the present invention provides a method for imaging thiols in mitochondria, including:

(a) injecting the two-photon fluorescent probe into a cell;

(b) the injected two-photon fluorescent probe reacting with thiols in mitochondria and emitting fluorescence; and (c) observing the fluorescence by two-photon microscopy.

Other features and aspects of the present invention will be apparent from the following detailed description, drawings and claims.

BRIEF DESCRIPTION OF THE DRAWINGS

The above and other objects, features and advantages of the present invention will now be described in detail with reference to certain exemplary embodiments thereof illustrated in the accompanying drawings which are given hereinbelow by way of illustration only, and thus are not limitative of the invention.

DETAILED DESCRIPTION

Figure 1:
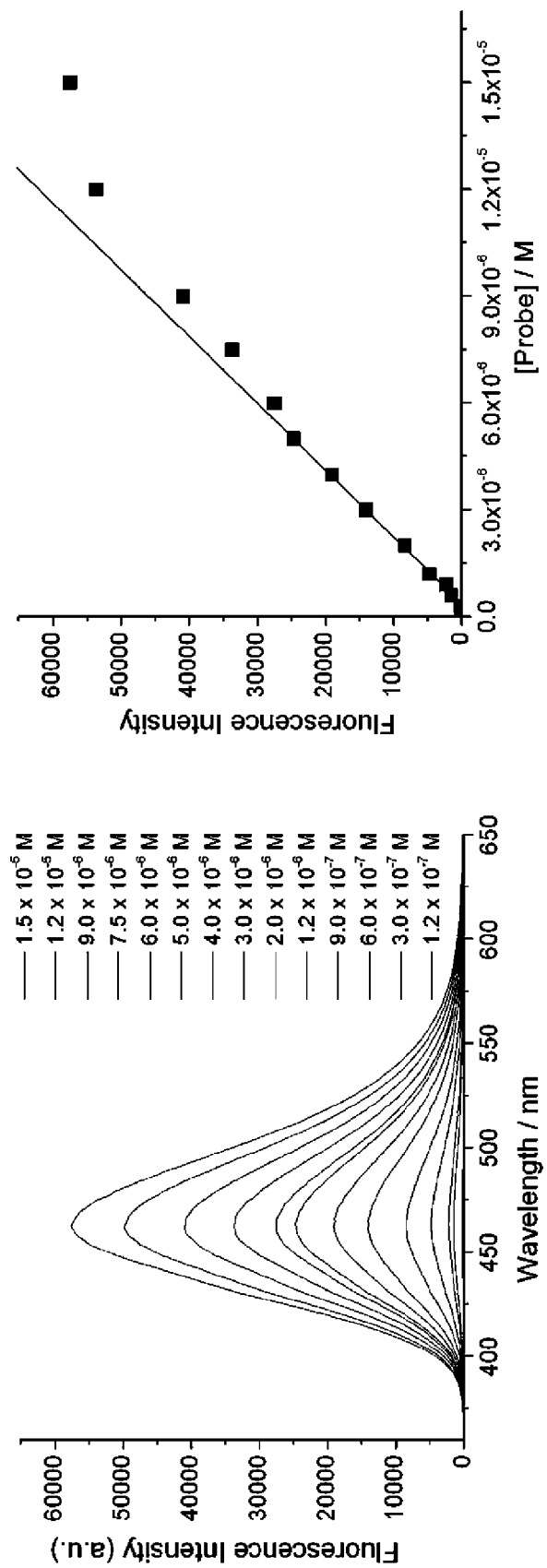
FIG. 1 shows (a) one-photon fluorescence spectra and (b) a plot of fluorescence intensity against the concentration of a two-photon fluorescent probe in a buffer (30 mM MOPS, 100 mM KCl, pH 7.4). The excitation wavelength was 340 nm.

Hereinafter, reference will now be made in detail to various embodiments of the present invention, examples of which are illustrated in the accompanying drawings and described below. While the invention will be described in conjunction with exemplary embodiments, it will be understood that the present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

The present invention relates to a ratiometric fluorescent probe (hereinafter, SSH-Mito) which is selectively targeted to mitochondria, the representative active cellular organelles, and is capable of imaging the activity of thiols existing inside mitochondria in real time by two-photon microscopy (TPM), a method for preparing same and a method for of thiols in mitochondria using same.

Hereinafter, the present invention is described in detail.

The present invention provides a two-photon fluorescent probe (SSH-Mito) represented by Formula 1:

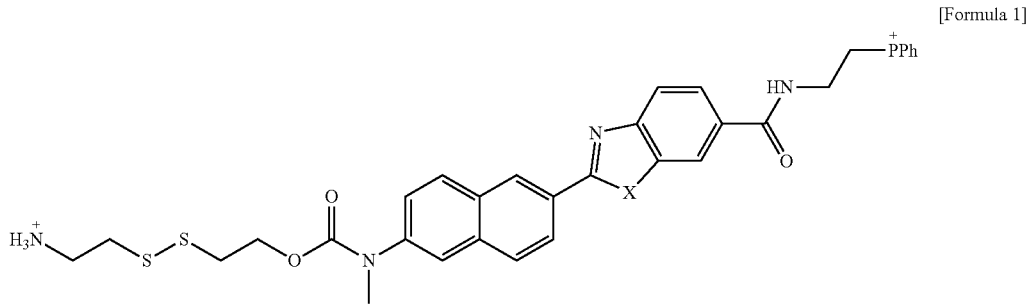

[Formula 1]

wherein X is S or O.

The two-photon fluorescent probe (SSH-Mito) of the present invention is prepared by introducing a triphenylphosphonium (TPP) salt as a mitochondrial probe and a disulfide bond as a thiol reaction site into a two-photon fluorophore 6-(benzo[d]thiazol-2'-yl)-2-(N,N-dimethylamino)naphthalene (BTDAN). In the compound, the triphenylphosphonium (TPP) salt and the disulfide bond are separated as far as possible to minimize interactions between them.

The two-photon fluorescent probe of the present invention selectively dyes mitochondria among cellular organelles and the relative fluorescence intensity ($F_{yellow}/F_{blue}$) at 425-475 nm ($F_{blue}$) and 525-575 nm ($F_{yellow}$) is increased by about 42-77 fold upon reaction with thiols. Accordingly, it may be used as a fluorescent probe adequate for imaging the selectivity and activity of thiols.

The two-photon fluorescent probe of the present invention exhibits strong responses toward glutathione (GSH), cysteine (Cys), homocysteine (Hcy), dithiothreitol (DTT), 2-mercaptoethanol (2-ME), 2-aminoethanethiol (2-AET), etc. containing thiol groups, and negligible responses toward amino acids without thiol groups (Glu, Ser, Val, Met, Ala, Ile), metal ions (Na+, K+, Ca+, Mg2+, Zn2+) and $H_2O_2$. Also, the two-photon fluorescent probe of the present invention (SSH-Mito) is pH-insensitive at biologically relevant pH.

Unlike the existing one-photon fluorescent probes, the two-photon fluorescent probe of the present invention has a deep penetration depth of 90 μm or greater, more specifically 90-190 μm, and is capable of detecting thiols in mitochondria in a living cell and a living tissue at depths of 90-190 μm. In addition, owing to superior photostability in cells, the two-photon fluorescent probe of the present invention is capable of continuously detecting thiols for 60 minutes or longer, more specifically for 30-90 minutes. Accordingly, the two-photon fluorescent probe of the present invention can serve as a superior ratiometric fluorescent probe without interference from other biologically relevant analytes or pH.

The present invention also provides a method for preparing a two-photon fluorescent probe, including:

(a) dissolving a compound represented by Formula 2 and a compound represented by Formula 3 in nitrobenzene and stirring the resulting mixture to obtain a compound represented by Formula 4;

(b) reacting the compound represented by Formula 4 with a compound represented by Formula 5 to obtain a compound represented by Formula 6;

(c) mixing the compound represented by Formula 6 with pyridine and a compound represented by Formula 7, adding N,N-dimethylaminopyridine (DMAP) and stirring the resulting mixture to obtain a compound represented by Chemical Formula; and (d) dissolving the compound represented by Formula 8 in a solvent, stirring and evaporating the solvent:

[Formula 1]

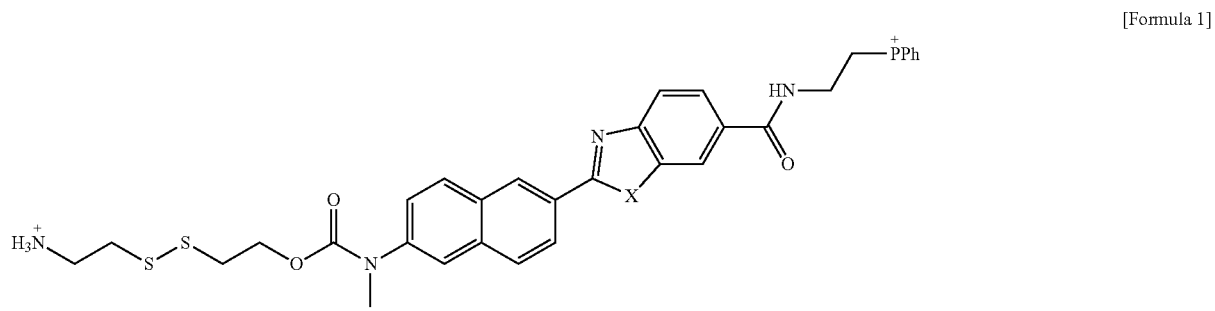

[Formula 2]

[Formula 3]

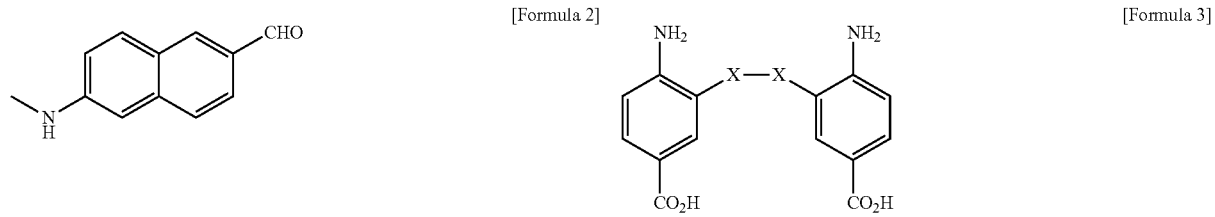

[Formula 4]

[Formula 5]

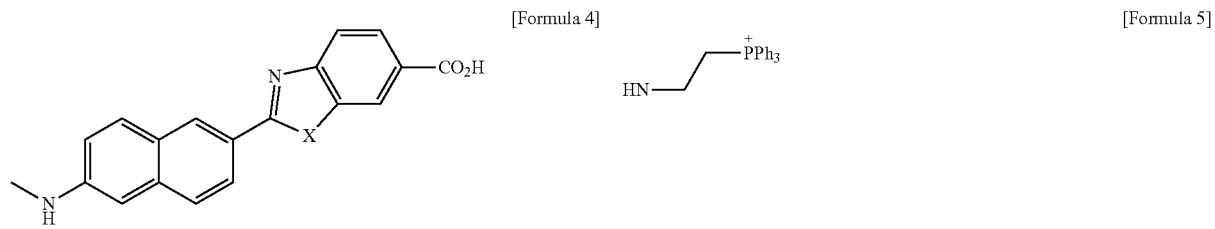

[Formula 6]

[Formula 7]

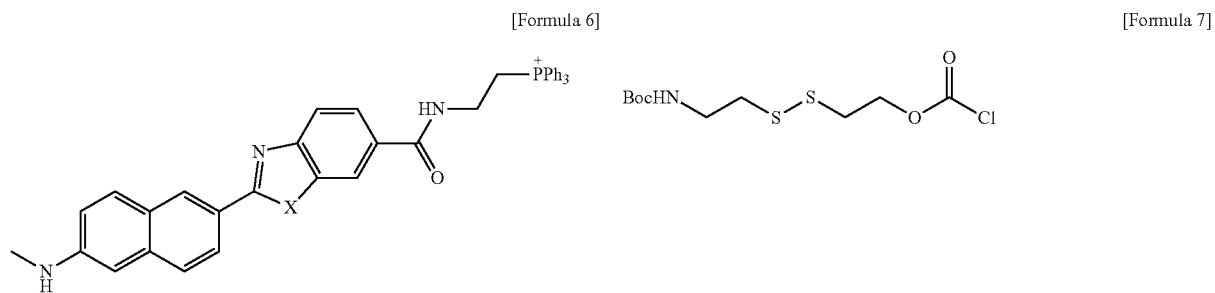

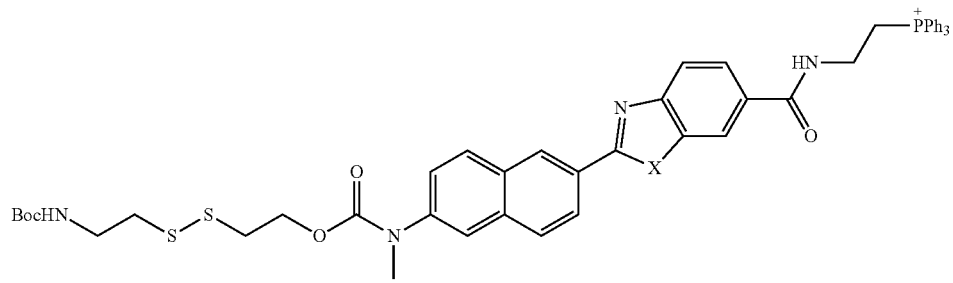

[Formula 8]

wherein X is S or O.

Finally, the present invention provides a method for imaging thiols in mitochondria, including:

(a) injecting the two-photon fluorescent probe into a cell;
(b) the injected two-photon fluorescent probe reacting with thiols in mitochondria and emitting fluorescence; and
(c) observing the fluorescence by two-photon microscopy.

In accordance with the present invention, the two-photon fluorescent probe can be selectively targeted to mitochondria in a cell simply by injecting the two-photon fluorescent probe at a very low concentration into the cell in (a). After the injection into the cell, two-photon excited fluorescence intensity is measured at 425-475 nm ($F_{blue}$) and 525-575 nm ($F_{yellow}$) at the same time in two channels upon excitation at 740 nm. The ratio of the fluorescence intensities ($F_{yellow}/F_{blue}$) is dependent on the thiol concentration. Upon reaction with thiols, the ratio of the fluorescence intensities ($F_{yellow}/F_{blue}$) is increased by about 42-77 fold, resulting in a high-resolution two-photon microscopic image. Two-photon microscopy (TPM) using two near-infrared photons of lower energy for excitation provides a number of advantages over one-photon microscopy, including increased penetration depth, localized excitation and prolonged observation time. The present invention allows effective imaging of the distribution and activity of thiols in mitochondria in a living cell or tissue using the imaging method.

EXAMPLES

The present invention will be described in more detail through examples. The following examples are for illustrative purposes only and it will be apparent to those skilled in the art not that the scope of this invention is not limited by the examples.

Example 1

Synthesis of Two-Photon Fluorescent Probe (SSH-Mito)

Synthesis of SSH-Mito

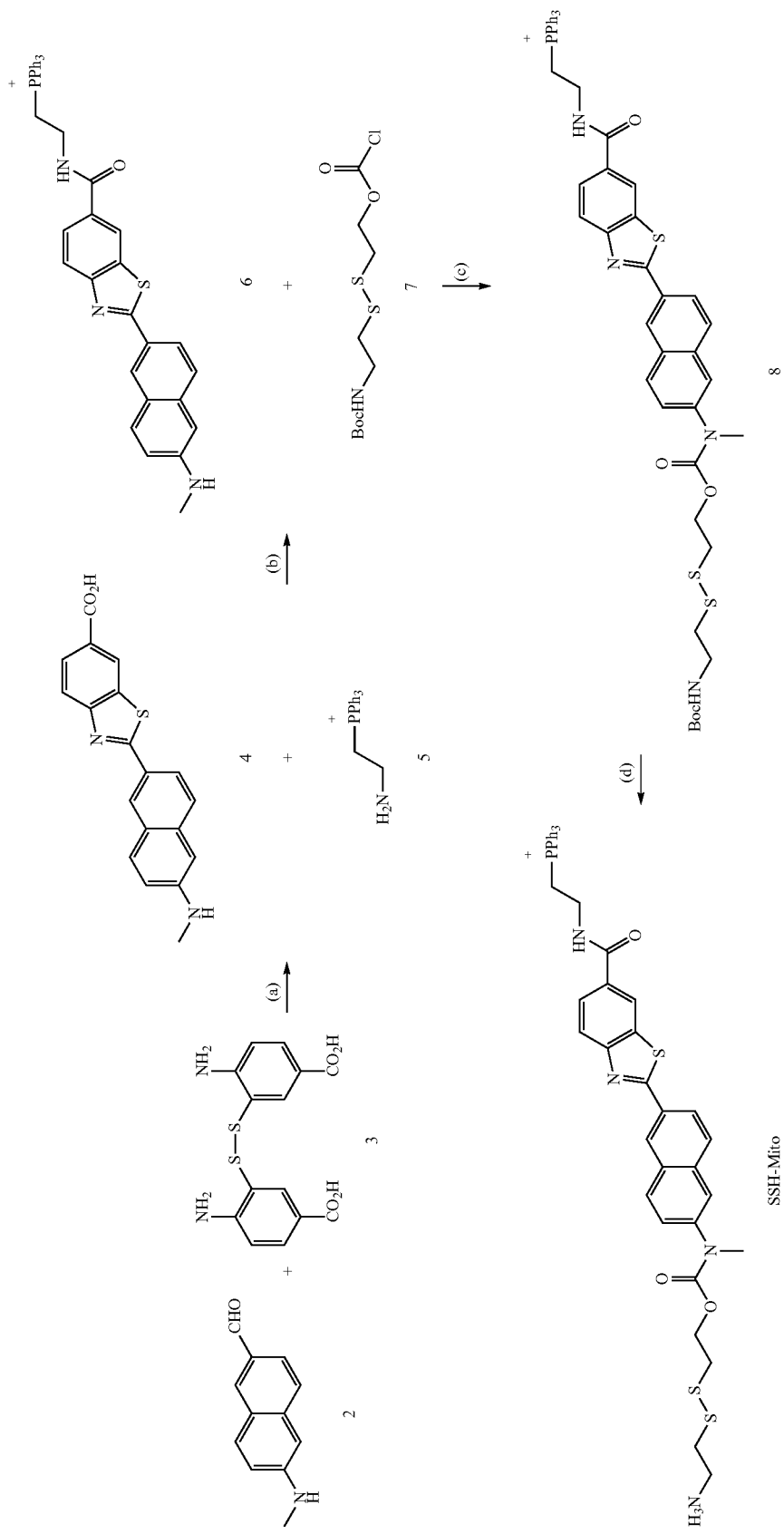

In Scheme 1, the compound represented by Formula 2[1], the compound represented by Formula 3[2], the compound represented by Formula 5[3] and the compound represented by Formula 7[4] were synthesized according to known methods ([1] H. M. Kim, B. H. Jeong, Ju-Y. Hyon, M. J. An, M. S. Seo, J. H. Hong, K. J. Lee, C. H. Kim, T. Joo, Seok-C. Hong, B. R. Cho, *J. Am. Chem. Soc.*, 2008, 130, 4246-4247; [2] K. Serdons, C. Terwinghe, P. Vermaelen, K. V. Laere, H. Kung, L. Mortelmans, G. Bormans, A. Verbruggen, *J. Med. Chem.* 2009, 52, 1428-1437; [3] B. E., A. B. Reitz, B. A. Duhl-Emswiler, *J. Am. Chem. Soc.*, 107, 226; [4] M. M. Pires, J. Chmielewski, *Org. Lett.* 2008, 10, 837-840).

The synthesis of SSH-Mito according to Scheme 1 is described in detail below.

(1) Synthesis of Compound Represented by Formula 4

The compound represented by Formula 3 (0.5 g, 1.48 mmol) and the compound represented by Formula 2 (0.55 g, 2.97 mmol) were dissolved in nitrobenzene (30 mL) and the reaction mixture was stirred at 180° C. under nitrogen atmosphere for 6 hours. After cooling to room temperature, hexane (50 mL) was added and the precipitate obtained was filtered off and washed with diethyl ether. The residue was digested with boiling THF (30 mL) and the insoluble impurities were removed by filtration. The filtrate was evaporated and the crude product was triturated with diethyl ether, filtered and dried in vacuo to afford a pure compound represented by Formula 4 as yellow solid (yield: 0.44 g (44%); m.p. 264-266° C.).

$^1$H NMR (400 MHz, DMSO-$d_6$): δ 13.17 (br s, 1H), 8.72 (s, 1H), 8.43 (d, J=2.0 Hz, 1H), 8.06-8.05 (m, 2H), 8.00 (dd, J=8.8, 2.0 Hz, 1H), 7.82 (d, J=8.8 Hz, 1H), 7.71 (d, J=8.8 Hz, 1H), 7.03 (dd, J=8.8, 2.0 Hz, 1H), 6.72 (d, J=2.0 Hz, 1H), 6.46 (q, J=4.4 Hz, 1H), 2.81 (d, J=4.4 Hz, 3H).

$^{13}$C NMR (400 MHz, DMSO-$d_6$+CDCl$_3$): 171.9, 167.5, 157.1, 150.0, 137.8, 134.8, 130.2, 128.3, 127.9, 127.8, 126.9, 126.2, 125.5, 124.7, 124.4, 122.4, 119.7, 101.9, 30.3.

(2) Synthesis of Compound Represented by Formula 6

The compound represented by Formula 4 (0.20 g, 0.60 mmol), 1,3-dicyclohexylcarbodiimide (DCC, 0.15 g, 0.73 mmol) and 1-hydroxybenzotriazole (0.10 g, 0.74 mmol) were dissolved in CH$_2$Cl$_2$ (10 mL). The reaction mixture was stirred at room temperature for 1 hour under nitrogen. To this mixture, (2-aminoethyl)triphenylphosphonium bromide (compound represented by Formula 5, 0.23 g, 0.60 mmol) was added and the whole reaction mixture was stirred for 10 hours. The solvent was evaporated and the crude product was purified by column chromatography using 8% methanol in CHCl$_3$ as a mobile phase to afford a compound represented by Formula 6 as yellow solid (yield: 0.19 g (45%); m.p. 146-148° C.).

$^1$H NMR (400 MHz, CDCl$_3$): δ 9.63 (br t, 1H, amide-NH), 8.58 (s, 1H), 8.31 (s, 1H), 8.12 (dd, J=8.4, 1.2 Hz, 1H), 7.99 (d, J=8.4 Hz, 1H), 7.97 (d, J=8.4 Hz, 1H), 7.83-7.63 (m, 17H), 6.92 (dd, J=8.8, 2.0 Hz, 1H), 6.71 (d, J=2.0 Hz, 1H), 4.45 (br s, 1H), 4.03-3.92 (m, 4H), 2.91 (s, 3H).

$^{13}$C NMR (100 MHz, CDCl$_3$): δ 171.6, 167.2, 156.4, 148.8, 137.2, 135.3 (d, J=3 Hz), 134.7, 133.8 (d, J=10.6 Hz), 130.7 (d, J=12.9 Hz), 130.1, 129.5, 128.0, 126.7, 126.6, 126.1, 125.0, 122.3, 122.0, 118.9, 117.6 (d, J=85.7 Hz), 103.2, 34.2, 30.7, 23.1 (d, J=48.6 Hz).

$^{31}$P NMR (162 MHz, CDCl$_3$): δ 21.8 ppm.

(3) Synthesis of Compound Represented by Formula 8

After mixing the compound represented by Formula 6 (0.30 g, 0.42 mmol), pyridine (0.35 mL, 4.32 mmol) and the compound represented by Formula 7 (0.2 g, 0.63 mmol) in DMF (5 mL), a catalytic amount of N,N-dimethylaminopyridine (DMAP) was added and the whole reaction mixture was stirred at room temperature for 16 hours. The solvent was evaporated in vacuo and the crude product was purified by column chromatography using 6% methanol in CHCl$_3$ as a mobile phase to afford a compound represented by Formula 8 as yellow solid (yield: 0.09 g (21%); m.p. 130-134° C.).

$^1$H NMR (400 MHz, CDCl$_3$): δ 9.54 (br t, 1H, amide-NH), 8.69 (d, J=1.6 Hz, 1H), 8.55 (s, 1H), 8.20 (dd, J=8.8, 1.6 Hz, 1H), 8.19 (dd, J=8.8, 1.6 Hz, 1H), 8.07 (d, J=8.8 Hz, 1H), 7.94 (d, J=8.8 Hz, 1H), 7.89 (d, J=8.8 Hz, 1H), 7.87-7.65 (m, 16H), 7.52 (d, J=8.8 Hz, 1H), 4.96 (br t, 1H, Boc-NH), 4.42 (t, J=6.0 Hz, 2H), 4.09-3.98 (m, 4H), 3.44 (s, 3H), 3.41 (q, J=6.0 Hz, 2H), 2.93 (t, J=6.0 Hz, 2H), 2.77 (t, J=6.0 Hz, 2H), 1.43 (s, 9H).

$^{13}$C NMR (100 MHz, CDCl$_3$): δ 170.5, 166.9, 156.3, 155.2, 142.2, 135.3 (d, J=3 Hz), 135.09, 134.9, 133.8 (d, J=10.6 Hz), 131.3, 130.9, 130.7 (d, J=12.9 Hz), 130.0, 129.7, 128.7, 127.6, 126.4, 125.8, 125.1, 124.1, 122.9, 122.3, 117.6 (d, J=85.7 Hz), 64.0, 39.5, 38.9, 38.1, 37.6, 34.2, 31.9, 28.7, 23.3 (d, J=48.6 Hz).

$^{31}$P NMR (162 MHz, CDCl$_3$): δ 21.8 ppm.

(4) Synthesis of SSH-Mito

The compound represented by Formula 8 (70 mg, 0.0713 mmol) was dissolved in a cold (0° C.) solution of TFA/CH$_2$Cl$_2$=5/5 mL. The solution was stirred in the dark at 0° C. for 1 hour and then further stirred at room temperature for 2 hours. The solvent was removed in vacuo and the crude product was purified by prep-LC with a mixture of 30% eluent A (HPLC-grade water containing 0.1% TFA) and 70% eluent B (HPLC-grade CH$_3$CN containing 0.1% TFA) for 15 minutes, followed by a linear gradient to 55% eluent A and 45% eluent B, with a flow rate of 40 mL/min. After evaporation of the solvent, SSH-Mito was obtained as yellow solid (yield: 0.035 g (50%); m.p. 62-64° C.).

$^1$H NMR (400 MHz, CDCl$_3$/DMSO-$d_6$): δ 9.97 (br t, 1H, amide-NH), 8.52 (s, 1H), 8.49 (s, 1H), 8.43 (br s, 3H, NH$_3^+$), 8.14 (dd, J=8.8, 2.0 Hz, 1H), 8.02-8.00 (m, 2H), 7.88 (d, J=8.4 Hz, 1H), 7.84 (d, J=8.8 Hz, 1H), 7.77-7.70 (m, 9H), 7.65-7.60 (m, 7H), 7.43 (d, J=8.4 Hz, 1H), 4.33 (t, J=6.0 Hz, 2H), 3.88-3.78 (m, 4H), 3.36 (s, 3H), 3.14 (br t, 2H), 2.87 (br t, 4H).

$^{13}$C NMR (100 MHz, CD$_2$Cl$_2$): δ 172.7, 169.4, 157.9, 157.3, 144.2, 137.4, 137.1, 136.8, 135.4 (d, J=10.6 Hz), 132.9, 132.5 (d, J=12.9 Hz), 132.0, 131.4, 130.6, 129.6, 127.8, 127.5, 126.7, 124.6, 123.7, 119.4 (d, J=85.7 Hz), 65.8, 40.9, 39.7, 39.2, 36.8, 36.5, 33.8, 24.9.

$^{31}$P NMR (162 MHz, CD$_3$OD): δ 21.8 ppm.

HRMS (FAB$^+$): m/z calcd for [C$_{44}$H$_{43}$N$_4$O$_3$PS$_3$]$^{2+}$: 802.2224. found: 802.2219.

Test Example 1

Measurement of Water Solubility

A small amount of the two-photon fluorescent probe (SSH-Mito) prepared in Example 1 was dissolved in DMSO to prepare a stock solution ($1.0 \times 10^{-2}$ M). The solution was diluted to $6.0 \times 10^{-3}$ to $6.0 \times 10^{-5}$ M and added to a cuvette containing 3.0 mL of a buffer (30 mM MOPS, 100 mM KCl, pH 7.4) using a microsyringe. In all cases, the concentration of DMSO in water was maintained at 0.2%. Referring to FIG. 1, the plot of the fluorescence intensity versus the concentration of the two-photon fluorescent probe is linear at low concentrations but shows a downward curvature at higher concentrations. The maximum concentration in the linear region is determined as the solubility of the two-photon fluorescent probe. That is to say, the solubility of the two-photon fluorescent probe according to the present invention (SSH-Mito) in the buffer is ~5.0 μM, suggesting that the two-photon fluorescent probe according to the present invention is very effective in staining cells.

Test Example 2

Measurement of Photophysical Properties

Photophysical properties of the two-photon fluorescent probe (SSH-Mito) (Example 1) and the compound represented by Formula 6 were measured in MOPS buffer (30 mM MOPS, 100 mM KCl, pH 7.4). The result is shown in Table 1.

TABLE 1[a]

| Compound | $\lambda^{(1)}_{max}(10^{-4}\epsilon)$[b] | $\lambda^{fl}_{max}$[c] | $\Phi$[d] | $R_{max}/R_{min}$[e] | $\lambda^{(2)}_{max}$[f] | $\delta$[g] | $\Phi\delta$[h] |
|---|---|---|---|---|---|---|---|
| SSH-Mito | 338 (2.05) | 462 | 0.82 | 45 (40) | 740 | 95 | 80 |
| Compound No. 6 | 383 (1.50) | 545 | 0.12 | | 750 | 550 | 55 |

[a]All data were measured in MOPS buffer (30 mM MOPS, 100 mM KCl, pH 7.4) unless specified otherwise.
[b]$\lambda_{max}$ of one-photon absorption spectra in nm unit. The numbers in parentheses are molar extinction coefficients in $M^{-1}cm^{-1}$ unit.
[c]$\lambda_{max}$ of one-photon emission spectra in nm unit.
[d]Fluorescence quantum yield, ±15%.
[e]Emission ratio ($F_{525-575}/F_{425-475}$) conversion factor, ($R_{max}/R_{min}$), measured by one-photon processes before and 2 hours after addition of 10 mM GSH. The number in parentheses is a value measured by two-photon processes.
[f]$\lambda_{max}$ of two-photon excitation spectra in nm unit.
[g]Peak two-photon cross section per photon in $10^{-5}$ cm$^4$s unit, ±15%.
[h]Two-photon action cross section.

From in Table 1, the intrinsic spectroscopic properties of SSH-Mito and the change thereof upon reaction with thiols can be understood.

Test Example 3

Measurement of Thiol Selectivity of Two-Photon Fluorescent Probe

Figure 2:
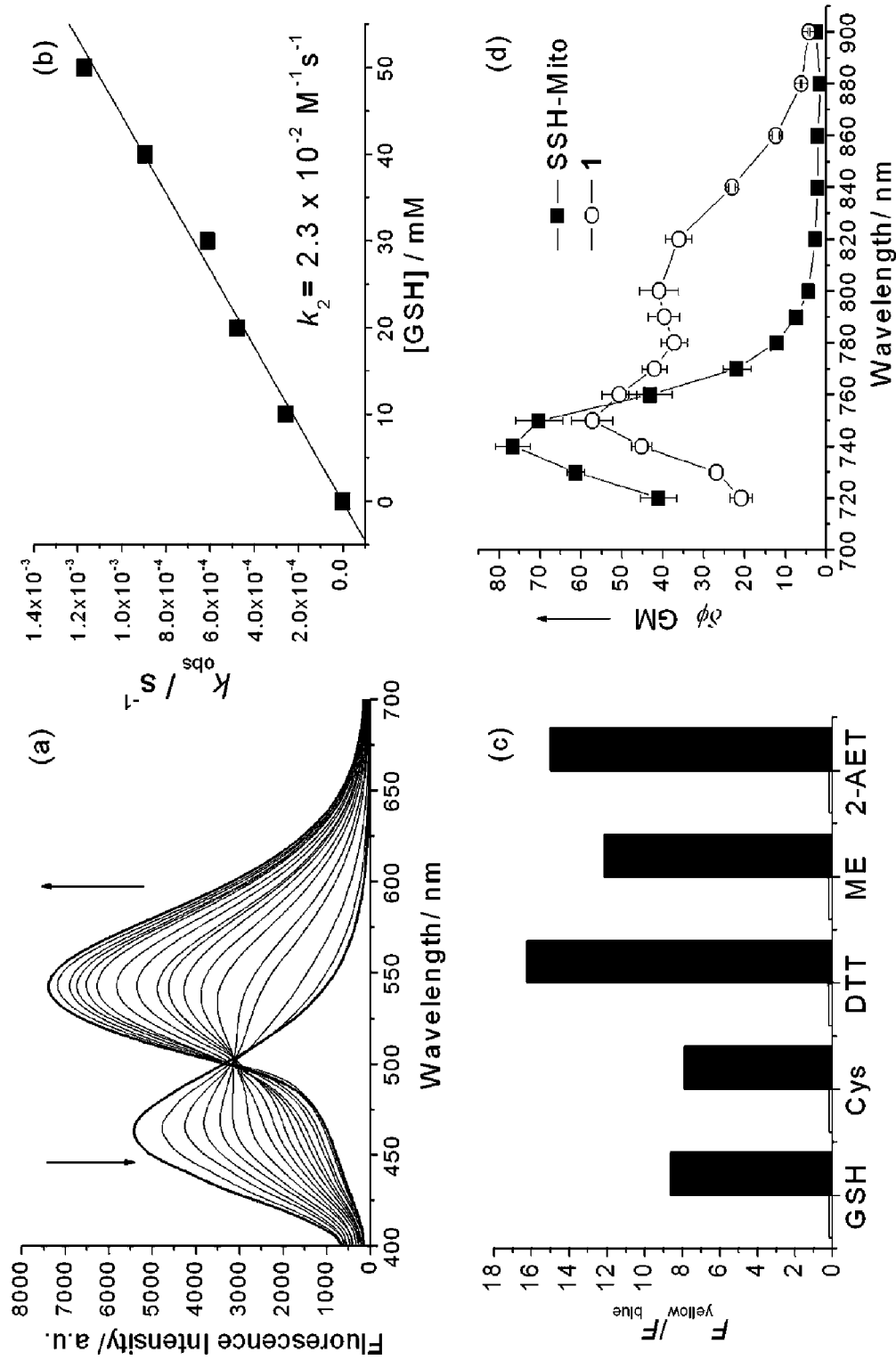
FIG. 2 shows (a) one-photon fluorescence response with time for the reaction of SSH-Mito (5 μM) with GSH (10 mM) in MOPS buffer (30 mM, pH=7.4), (b) a plot of $k_{obs}$ against the concentration of GSH, (c) fluorescence response of SSH-Mito toward GSH, Cys, DTT, 2-ME and 2-AET (The white and black bars represent the integrated fluorescence ratios ($F_{yellow}/F_{blue}$) of SSH-Mito before and 2 hours after addition of thiols, respectively) and (d) two-photon action spectra of SSH-Mito and a compound represented by Formula 7 (1) in MOPS buffer.
Figure 3:
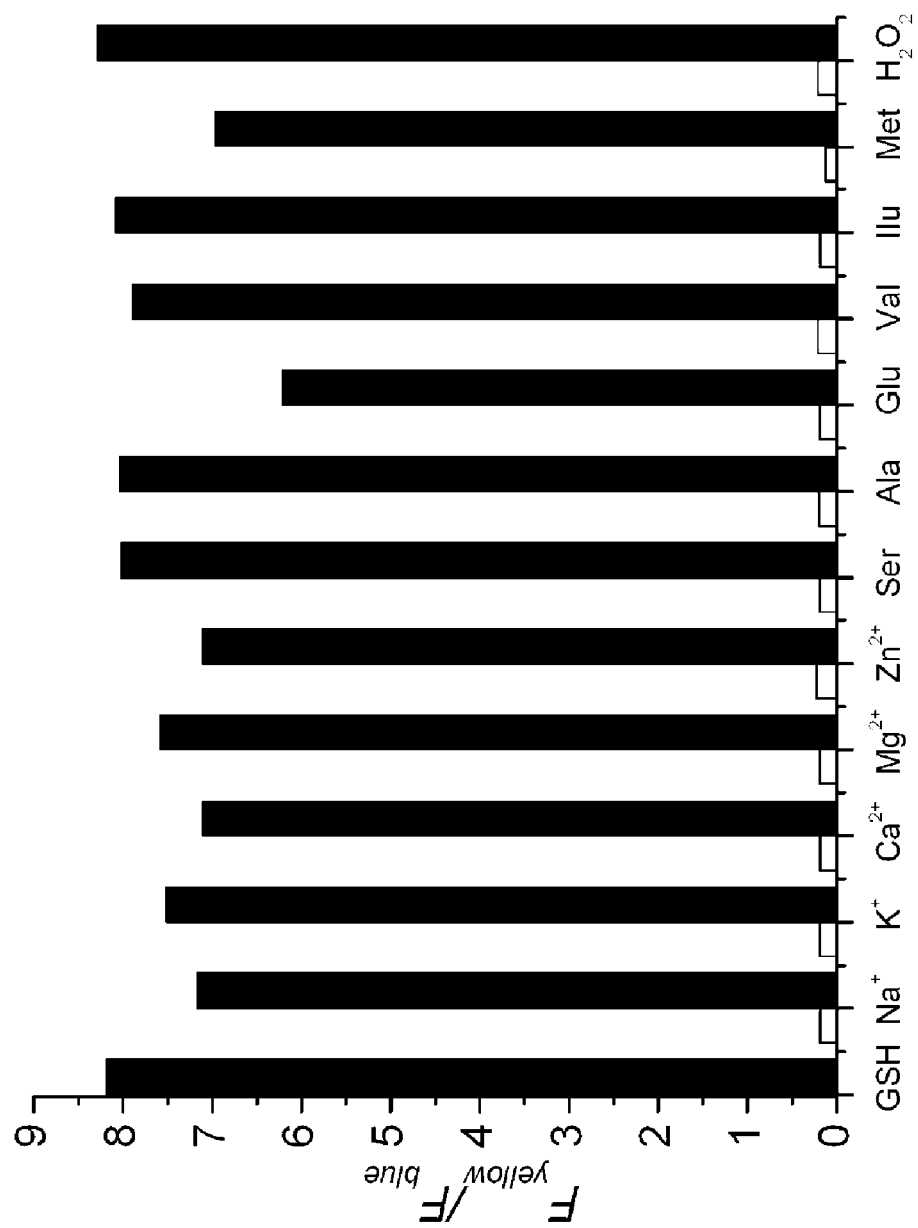
FIG. 3 shows fluorescence responses of SSH-Mito (5 μM) toward GSH and other analytes in MOPS buffer. White and black bars represent the relative fluorescence intensity ($F_{yellow}/F_{blue}$) of SSH-Mito (5 μM) in the presence of various analytes before and after addition of GSH, respectively. Each spectrum was acquired 2 hours after addition of various analytes at 37° C.

FIG. 3 shows relative fluorescence intensity of SSH-Mito (5 μM) in 30 mM MOPS buffer (100 mM KCl, 10 mM EGTA, pH 7.4) upon addition of 10 mM Na$^+$, K$^+$, Ca$^{2+}$, Mg$^{2+}$, Zn$^{2+}$, Ser, Ala, Glu, Val, Ilu, Met, H$_2$O$_2$ and GSH. White and black bars represent the relative fluorescence intensity before and after addition of GSH, respectively. Referring to FIG. 3, the two-photon fluorescent probe according to the present invention shows high selectivity for GSH than for Na$^+$, K$^+$, Ca$^{2+}$, Mg$^{2+}$, Zn$^{2+}$, Ser, Ala, Glu, Val, Ilu, Met and H$_2$O$_2$ (see FIG. 2 (c) and FIG. 3).

Figure 4:
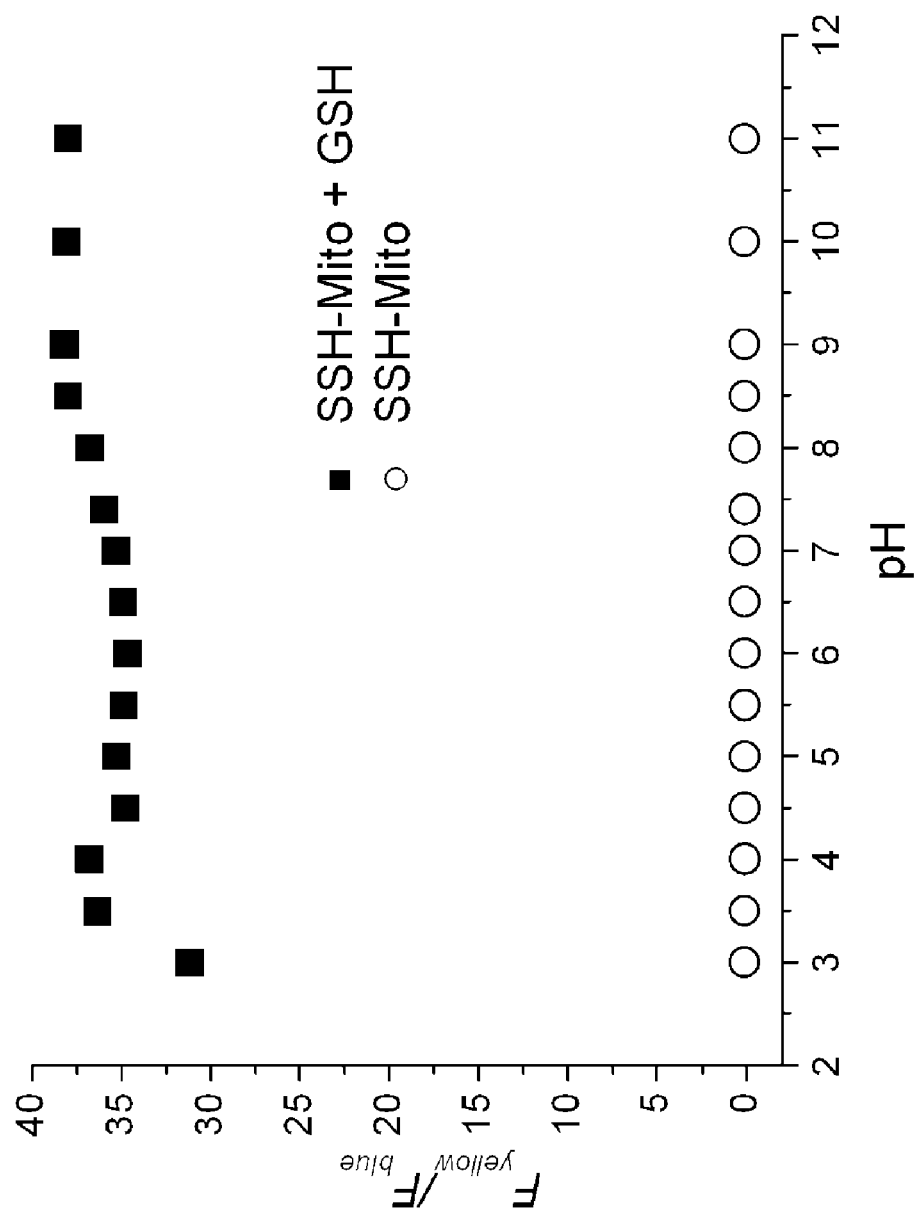
FIG. 4 shows the effect of pH on the fluorescence intensity of SSH-Mito (5 μM) in the absence (○) and presence (■) of 10 mM GSH in 3 mL of MOPS buffer (37° C., 2 hours). The excitation wavelength was 380 nm.

FIG. 4 shows the effect of pH on the fluorescence intensity of SSH-Mito (5 μM) in the absence (○) and presence (■) of 10 mM GSH in 3 mL of MOPS buffer. That is to say, the two-photon fluorescent probe according to the present invention exhibits high fluorescence intensity at biologically relevant pH in a pH-independent manner.

Accordingly, it can be seen that the two-photon fluorescent probe according to the present invention has very high selectivity for GSH, is pH-insensitive at biologically relevant pH and is very useful as a two-photon dye for thiols.

Test Example 4

Measurement of Mitochondrial Selectivity of Two-Photon Fluorescent Probe

Figure 5:
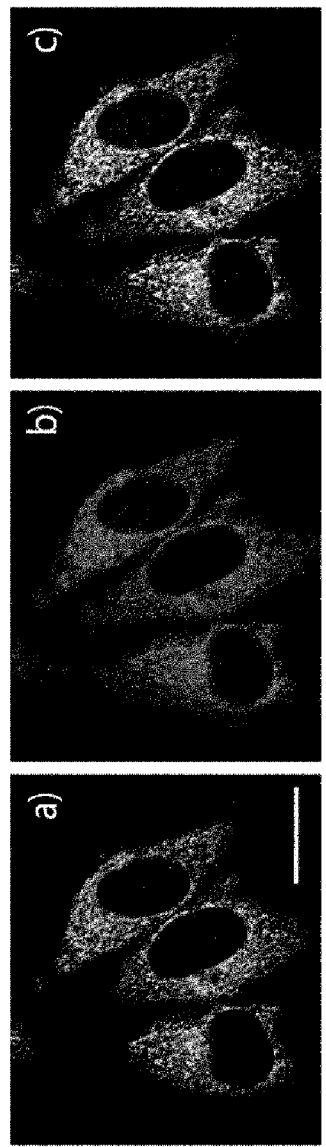
FIG. 5 shows (a) TPM and (b) OPM images of HeLa cells co-labeled with SSH-Mito (5 μM) and (b) MitoTracker Red FM (5 μM) for 30 minutes at 37° C. and (c) a co-localized image of (a) and (b). The wavelengths for one-photon and two-photon excitation were 514 and 740 nm, respectively, and the emission was collected at 425-575 nm (SSH-Mito) and 600-700 nm (MitoTracker Red FM). Scale bar: 30 μm. The cells shown are representative images obtained from repeated experiments (n=5).

To confirm whether the two-photon fluorescent probe of the present invention exhibits specific selectivity for mitochondria, a colocalization experiment was conducted using SSH-Mito and MitoTracker. In order to confirm whether the strong green fluorescence image stained with the two-photon fluorescent probe (SSH-Mito) shown in FIG. 5 (a) is actually the image of, HeLa cells were stained with MitoTracker Red (Invitrogen), a well-known one-photon fluorescent probe for mitochondria, and thus obtained one-photon red fluorescence image (FIG. 5 (b)) was overlapped with the green fluorescence image (FIG. 5 (c)). As seen from FIG. 5 (c), the two images (FIG. 5 (a), (b)) obtained by staining with the two dyes correspond well to each other. Also, the Pearson's colocalization coefficient of SSH-Mito and MitoTracker calculated using the Autoquant X2 software was 0.85, indicating that SSH-Mito exists predominantly in mitochondria.

Accordingly, it can be seen that the two-photon probe according to the present invention can correctly image mitochondria.

Test Example 5

Imaging of Thiol Activity in Mitochondria by Two-Photon Microscopy Using Two-Photon Fluorescent Probe It was tested if the two-photon fluorescent probe of the present invention can monitor the change of thiols in a living cell.

Figure 6:
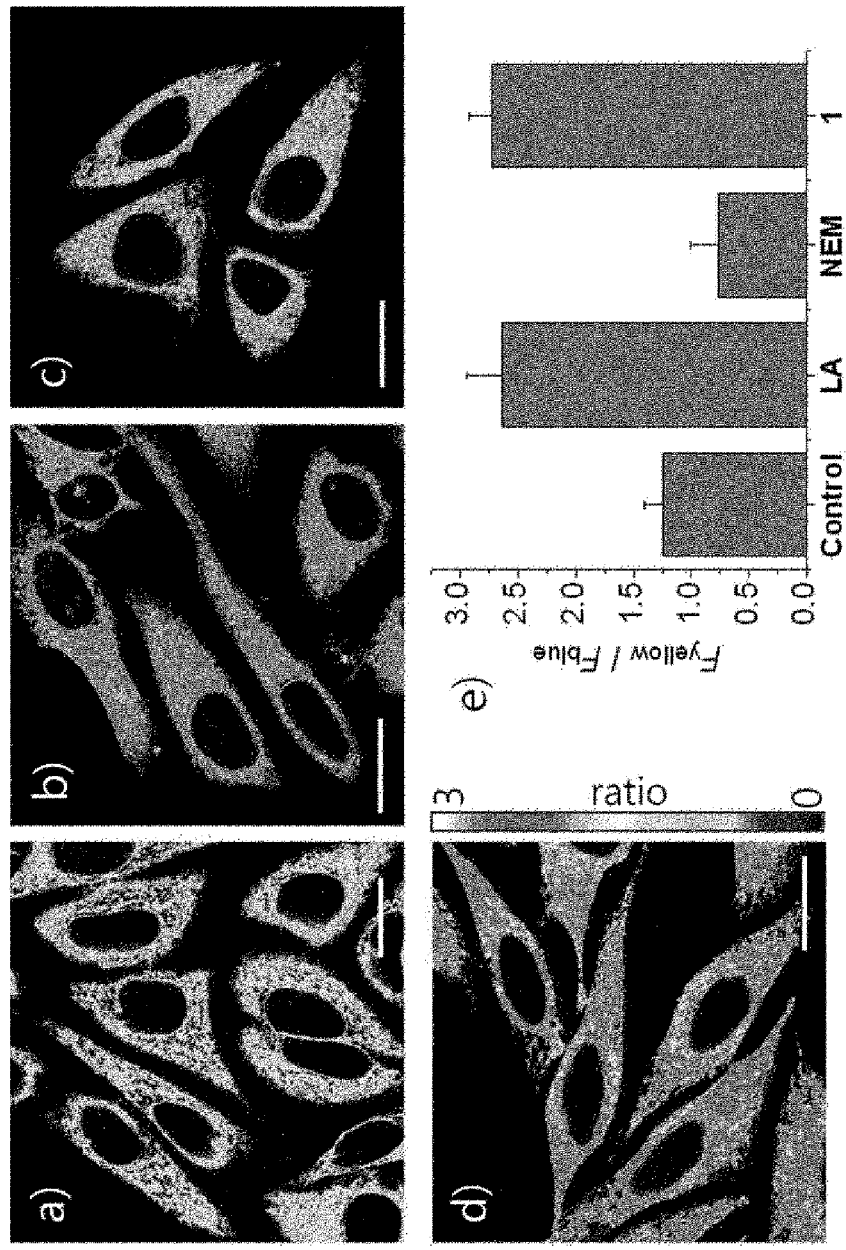
FIG. 6 shows (a-d) pseudocolored ratiometric TPM images of HeLa cells incubated with 5 μM (a) SSH-Mito and (d) a compound represented by Formula 7 (1) and the cells pretreated with (b) lipoic acid (500 μM) for 1 day and with (c) NEM (100 μM) for 30 minutes before labeling with SSH-Mito. (e) shows average fluorescence intensity ($F_{yellow}/F_{blue}$) of (a)-(d). The images were acquired using 740 nm excitation and fluorescence emission windows of 425-475 nm (blue) and 525-575 nm (yellow). Scale bar: 20 μm. The cells shown are representative images obtained from repeated experiments (n=5).

Under two-photon (TP) excitation at 740 nm, the image of HeLa cells labeled with two-photon fluorescent probe of the present invention (SSH-Mito) exhibited an average emission ratio of 1.24 (FIG. 6 (a), (e)). When the cells were pre-incubated for 1 day with α-lipolic acid which increases GSH production (FIG. 6 (b)), the $F_{yellow}/F_{blue}$ ratio increased to 2.64. And, when treated with N-ethylmaleimide (NEM), a well-known thiol blocking agent, the $F_{yellow}/F_{blue}$ ratio decreased to 0.77 (FIG. 6 (c)). These findings demonstrate that the two-photon fluorescent probe of the present invention (SSH-Mito) is capable of detecting thiols in living cells for a long time with minimized interference from competing metal ions, pH, etc.

Test Example 6

Measurement of Cytotoxicity

Figure 7:
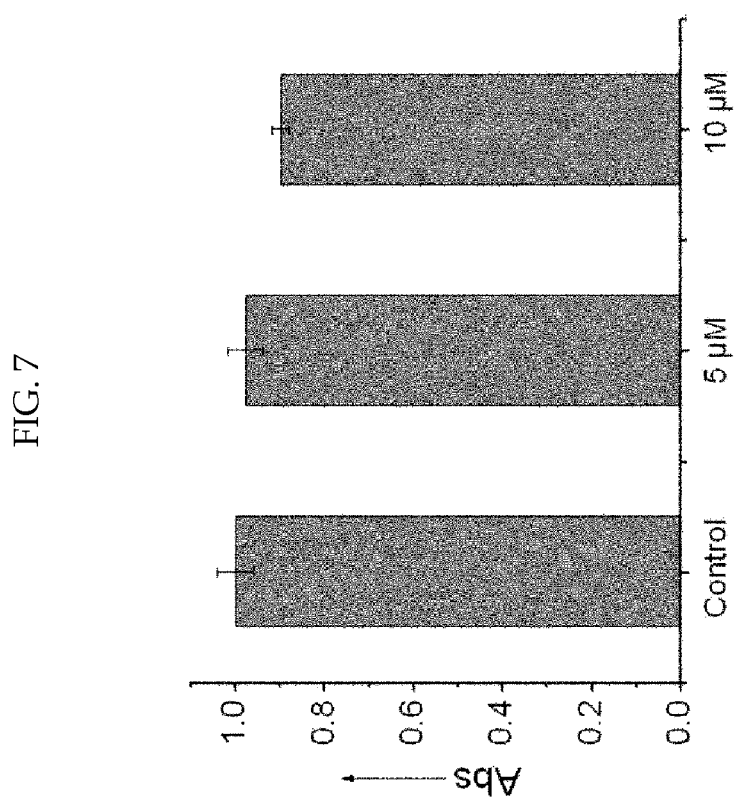
FIG. 7 shows viability of HeLa cells in the presence of SSH-Mito measured using a CCK-8 kit. The cells were incubated with SSH-Mito for 2 hours.

In order to confirm that the two-photon fluorescent probe of the present invention exhibits no cytotoxicity, the viability of HeLa cells was measured using the CCK-8 kit (Cell Counting Kit-8, Dojindo, Japan) following the protocol described in the manual. The result is shown in FIG. 7. It was confirmed that SSH-Mito is adequate for detecting thiols in living cells.

Test Example 7

Imaging of Rat Hippocampal Slices by Two-Photon Microscopy Using Two-Photon Fluorescent Probe In order to investigate the utility of two-photon fluorescent probe of the present invention in tissue imaging, rat hippocampal slices were monitored.

Figure 8:
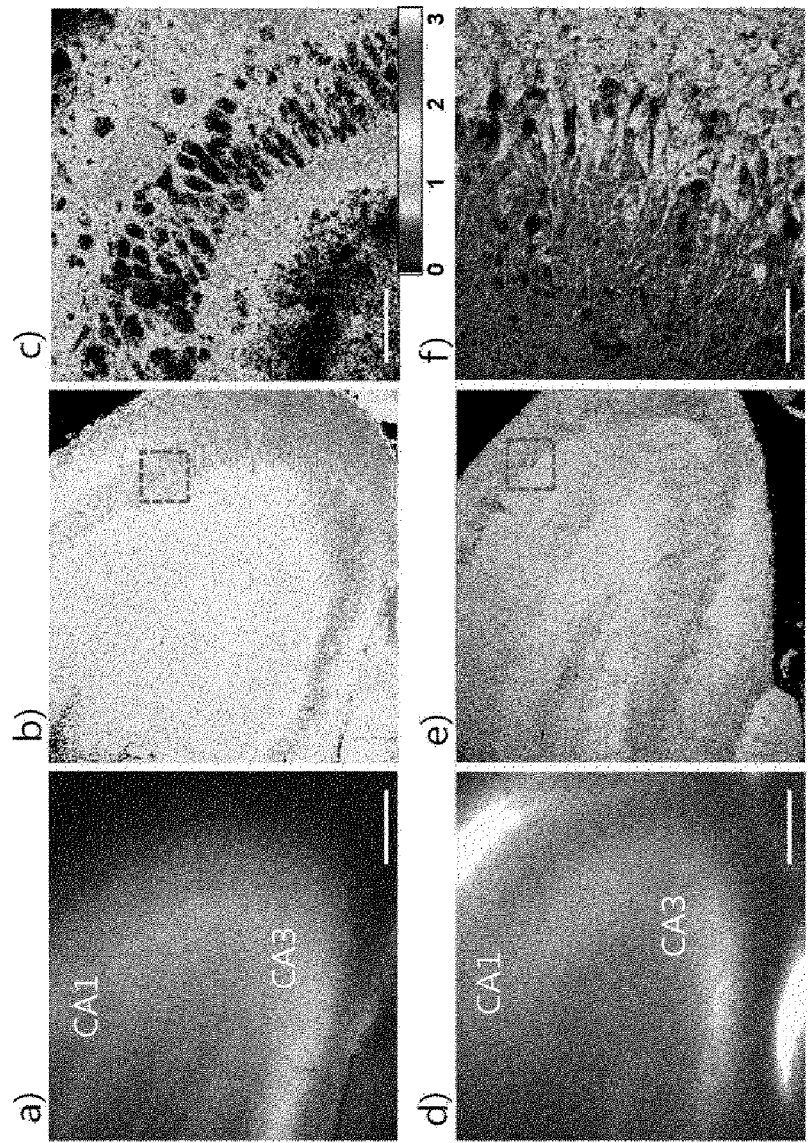
FIG. 8 shows images of rat hippocampal slices stained with 20 μM SSH-Mito for 2 hours. (a, d) Bright-field images of the CA1 and CA3 regions. (b, e) Ratiometric TPM images of rat hippocampal slices that were (b) not treated and (e) pretreated with NEM (100 μM) for 30 minutes before labeling with SSH-Mito. Ten TPM images were accumulated along the z-axis direction at depths of about 90-190 μm (10×). (c, f) Enlarged (40×) images of the red boxes in (b) and (e) at a depth of 120 μm. The two-photon excited fluorescence (TPEF) was collected in two channels (blue=425-475 nm, yellow=525-575 nm) upon excitation at 740 nm with a femtosecond (fs) pulse. Scale bars: 300 μm (a, d) and 75 μm (c, f)).

The bright-field images of the rat hippocampal slices revealed the CA1 and CA3 regions (FIG. 8 (a), (d)). Since the structure of the brain tissue is known to be inhomogeneous throughout its entire depth, 10 TPM images were obtained at depths of 90-190 μm and they were combined to visualize the overall thiol distribution. It was revealed that thiols are not evenly distributed in both the CA1 and CA3 regions (FIG. 8 (b)). Moreover, the image at higher magnification clearly showed the thiol (RSH) distribution in the individual cells in the CA1 region with an average emission ratio of 1.66 at a depth of 120 μm (FIG. 8 (c)). When the tissue was treated with 100 μM NEM for 30 minutes, the ratio decreased to 0.85 (FIG. 8 (f)). These findings demonstrate that even the change in the emission ratio deep in the tissue slice is detectable.

The above experimental results demonstrate that the two-photon fluorescent probe according to the present invention (SSH-Mito) is capable of very effectively detecting thiols existing in a living tissue, particularly in mitochondria, at depths of 90-190 μm by TPM.

The probe according to the present invention, having two probes introduced in one molecule, can selectively dye mitochondria and emit intense fluorescence by reacting with thiols. Also, thanks to superior water solubility and small molecular weight, it can be easily loaded into a cell. In addition, since it can selectively detect thiols in mitochondria in a living cell and a living tissue at a depth of 90-190 μm for 60 minutes or longer, it can be used to image the distribution and activation of thiols in a living cell or an intact living tissue.

The present invention has been described in detail with reference to specific embodiments thereof. However, it will be appreciated by those skilled in the art that various changes and modifications may be made in these embodiments without departing from the principles and spirit of the invention, the scope of which is defined in the appended claims and their equivalents.

What is claimed is:

1. A two-photon fluorescent probe represented by Formula 1:

[Formula 1]

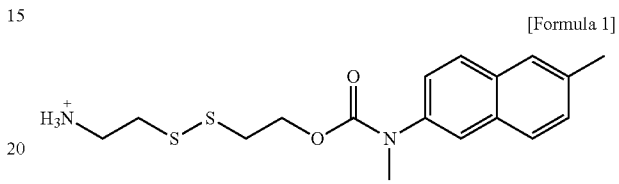

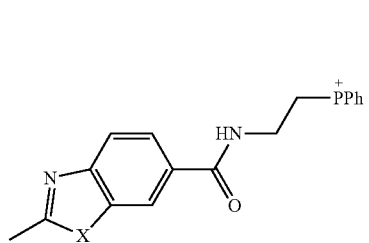

wherein X is S or O.

2. A method for preparing a two-photon fluorescent probe represented by Formula 1, comprising:
    dissolving a compound represented by Formula 2 and a compound represented by Formula 3 in nitrobenzene and stirring the resulting mixture to obtain a compound represented by Formula 4;
    reacting the compound represented by Formula 4 with a compound represented by Formula 5 to obtain a compound represented by Formula 6;
    mixing the compound represented by Formula 6 with pyridine and a compound represented by Formula 7, adding N,N-dimethylaminopyridine (DMAP) and stirring the resulting mixture to obtain a compound represented by Chemical Formula; and
    dissolving the compound represented by Formula 8 in a solvent, stirring and evaporating the solvent:

[Formula 1]

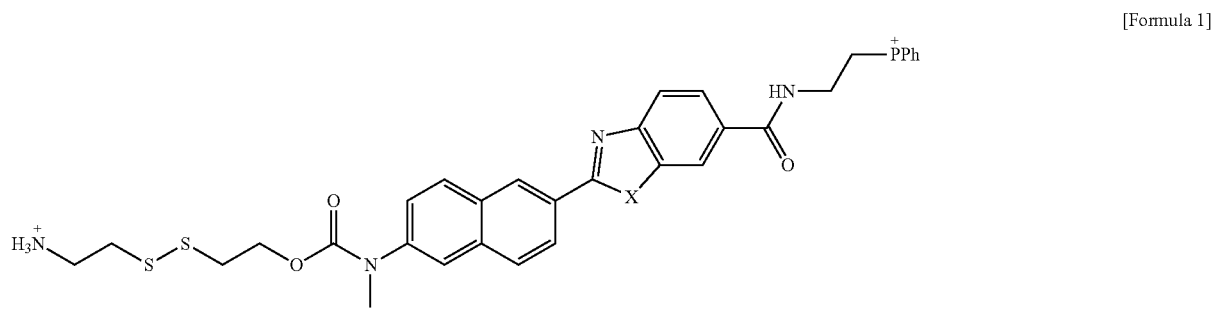

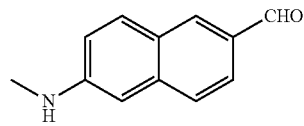

[Formula 2]

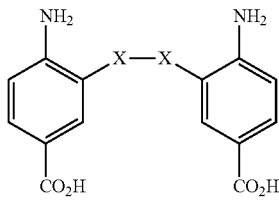

[Formula 3]

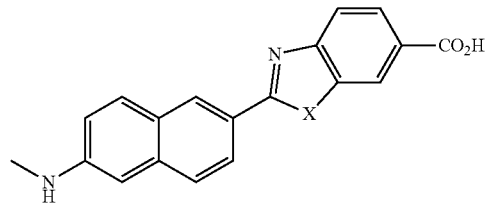

[Formula 4]

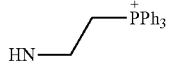

[Formula 5]

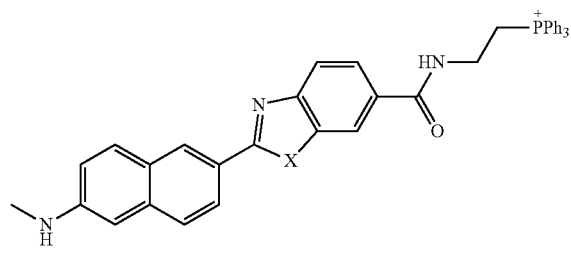

[Formula 6]

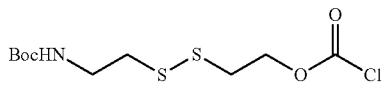

[Formula 7]

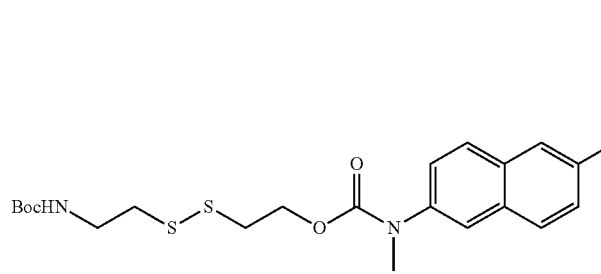

[Formula 8]

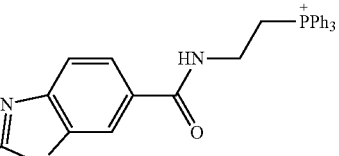

wherein X is S or O.

3. A method for imaging thiols in mitochondria, comprising:
  injecting the two-photon fluorescent probe according to claim 1 into a cell;
  the injected two-photon fluorescent probe reacting with thiols in mitochondria and emitting fluorescence; and
  observing the fluorescence by two-photon microscopy.

* * * * *